Figure 1:
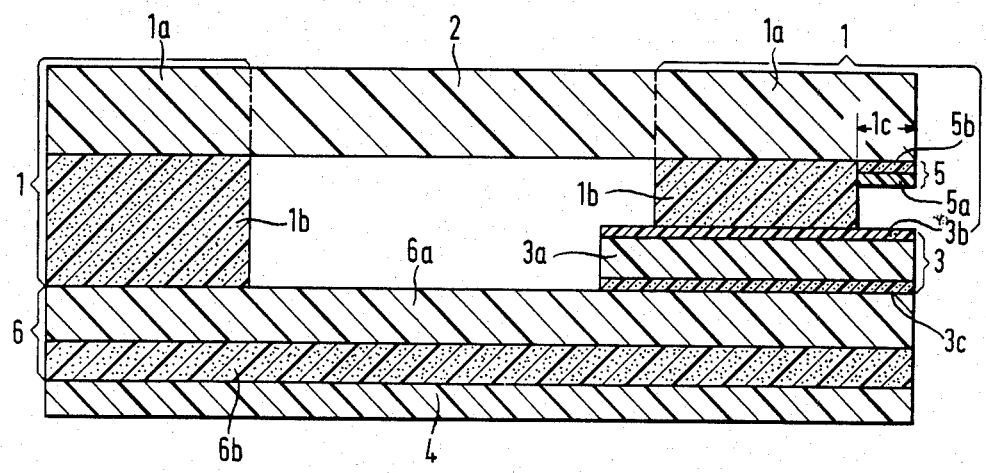

United States Patent [19]

Szonn et al.

[11] Patent Number: 4,522,853

[45] Date of Patent: Jun. 11, 1985

[54] ELASTIC DIAPER-PANTS FASTENING

[75] Inventors: Bodo Szonn, Kisdorf; Karl Schäfer; Alfred Malskeit, both of Hamburg, all of Fed. Rep. of Germany

[73] Assignee: Beiersdorf Aktiengesellschaft, Hamburg, Fed. Rep. of Germany

[21] Appl. No.: 487,428

[22] Filed: Apr. 21, 1983

[30] Foreign Application Priority Data

Apr. 30, 1982 [DE] Fed. Rep. of Germany ... 8212480[U]

[51] Int. Cl.³ .............................................. G61F 13/16
[52] U.S. Cl. ........................................ 428/40; 428/99; 604/389; 604/390
[58] Field of Search ............................... 604/389, 390; 428/40–42, 99

[56] References Cited

U.S. PATENT DOCUMENTS 3,930,503  1/1976  Fritsch ................................. 604/389
4,074,716  2/1978  Schaar ................................. 604/390

FOREIGN PATENT DOCUMENTS 49-54273  7/1973  Japan ................................. 604/389

Primary Examiner—George F. Lesmes
Assistant Examiner—Nancy A. B. Swisher
Attorney, Agent, or Firm—Sprung, Horn, Kramer & Woods

[57] ABSTRACT

The invention relates to a self-adhesive elastic diaper-pants fastening with an intermediate elastic piece and non-elastic adhesion ends. The fastening is so effected that the adhesion ends will not stretch and will adhere to the material out of which the pants are made tightly enough that the tensions produced by the wearer's movements will not cause them to become loose of their own accord.

2 Claims, 8 Drawing Figures

ELASTIC DIAPER-PANTS FASTENING

The invention relates to a self-adhesive elastic diaper-pants fastening with an intermediate elastic piece and non-elastic adhesion ends.

Diaper pants are known. German OS No. 2 233 359 for example discloses a semi-elastic strip fastening with a freely stretching intermediate elastic section and two non-stretching non-elastic end sections. There are, however, considerable practical drawbacks to this fastening in that the area to which the fastening is attached rips easily.

The objective of the present invention is to improve the self-adhesive elastic diaper-pants fastening with an intermediate elastic piece and non-elastic adhesion ends that is known as state of the art in such a way as to eliminate these drawbacks completely or to the extent that the fastening can be easily, practically, and reliably established. In particular, the adhesion ends will not stretch and will adhere to the material out of which the pants are made tightly enough that the tensions produced by the wearer's movements will not cause them to come loose of their own accord.

The invention accordingly concerns a fastening of the aforesaid type, characterized by (a) adhesion ends (1) with an intermediate elastic piece (2), (b) a non-stretching base (1a), on which is mounted a pressure-sensitive adhesive (1b), in the vicinity of each adhesion end (1), (c) a strip that is free of pressure-sensitive adhesive and functions as a grip (1c), provided if need be with a grip reinforcement (5) consisting of a base (5a) and a pressure-sensitive adhesive (5b), at the edge of one of the two adhesion ends (1), (d) a reinforcing strip (6) consisting of a base (6a) and a pressure-sensitive adhesive (6b), (e) an adhesive-resistant layer (3b) that is mounted either directly on the reinforcing strip (6) or on a transition strip (3) that rests on the reinforcing strip with a base (3a) and a pressure-sensitive adhesive (3c), with the adhesive-resistant layer (3b) positioned on the side of the reinforcing strip (6) that lies under the adhesion end (1) that has the grip (1c) and extending from 2-5 mm into the vicinity of the reinforcing strip (6) that lies under the intermediate elastic piece (2), and (f) a cover (4) that extends over the whole width of the fastening.

The longer adhesion end, the one with the grip (1c), adheres to the rear of the transition strip in such a way that it can easily be separated by the user but will not come loose prematurely on its own accord as the result of light mechanical stress. The adhesive on the reinforcing strip should also adhere tightly to the material from which the diaper is made.

The fastening in accordance with the invention allows a reliable and easily established connection for securing diaper pants in which the flexible intermediate elastic piece will readily follow the breathing and other movements of the wearer.

Other advantages as compared to the known, rigid systems are that (1) positioning the adhesion end (1) with the grip to the matching end of the diaper requires little care, (2) diagonal tensile strains during fastening do not cause the attachment strip (intermediate piece) to rip, (3) the adhesive-free intermediate elastic piece keeps the skin of the wearer from coming into contact with adhesive, and (4) the use of a reinforcement strip transmits the stresses that occur during fastening uniformly to both sides of the edge of the diaper pants, largely eliminating the risk of damage, a rip in the edge of the pants for example.

Further details and preferred embodiments will be specified with reference to the drawings.

Figure 2:
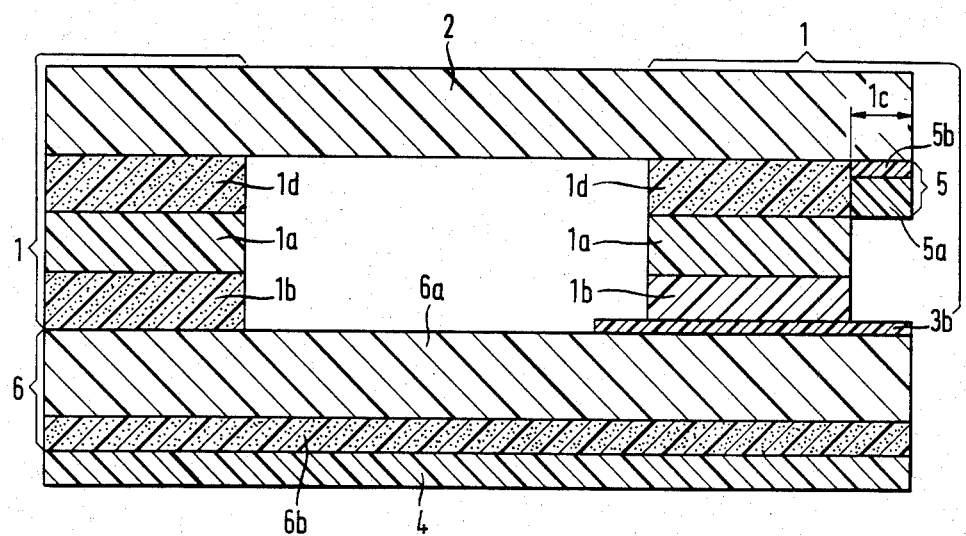
Figure 3:
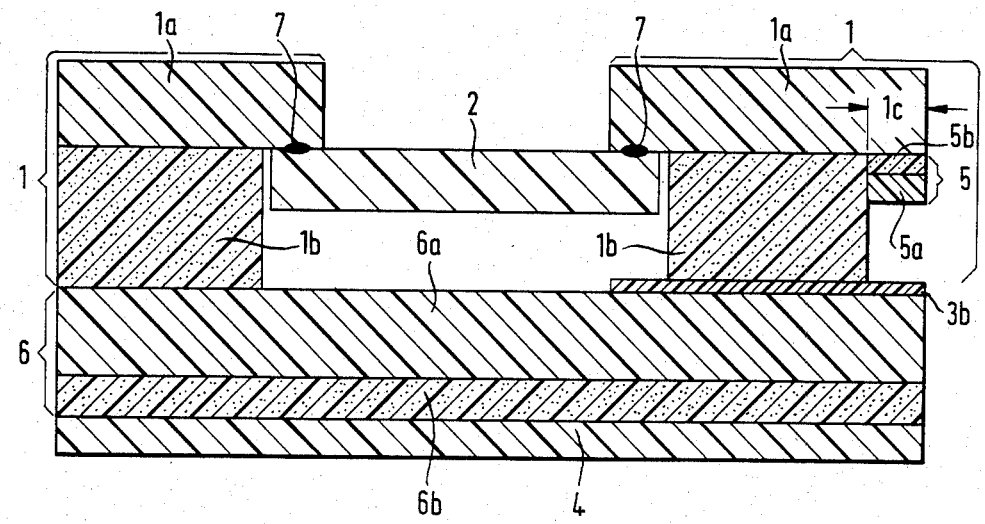
Figure 4:
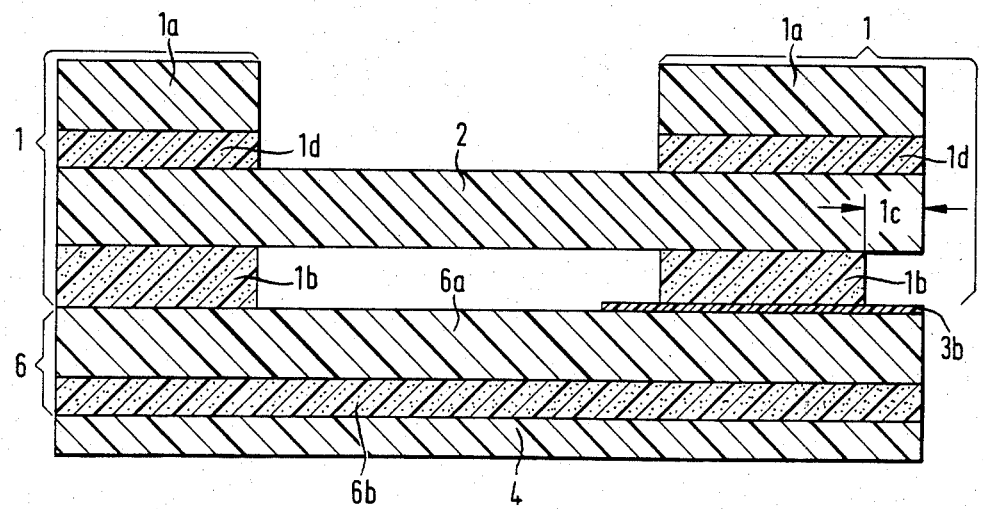
Figure 5A:
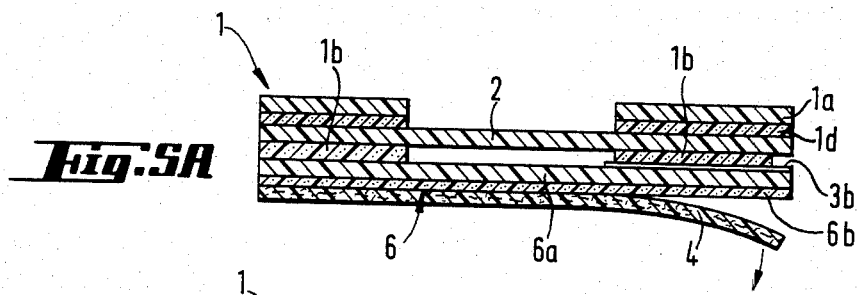
Figure 5B:
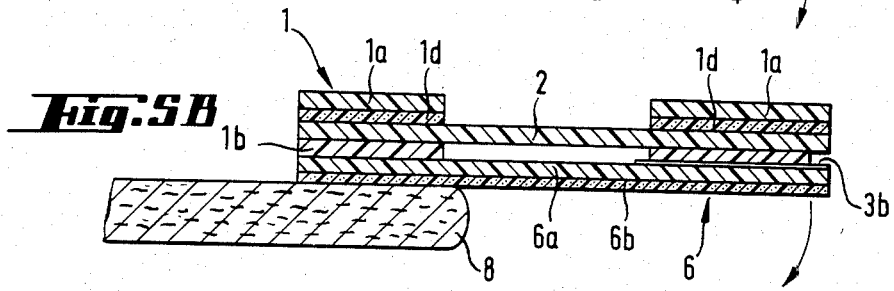
Figure 5C:
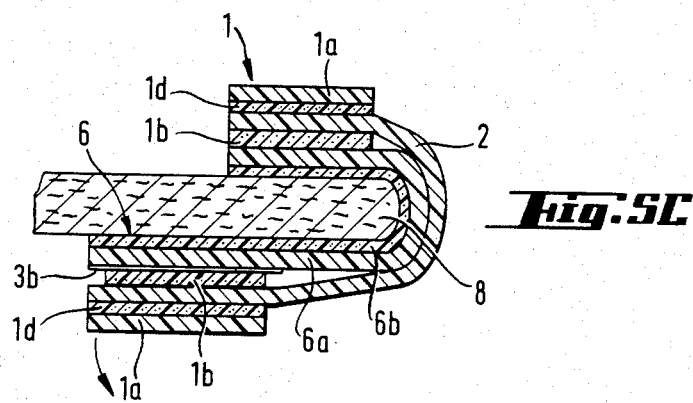
Figure 5D:
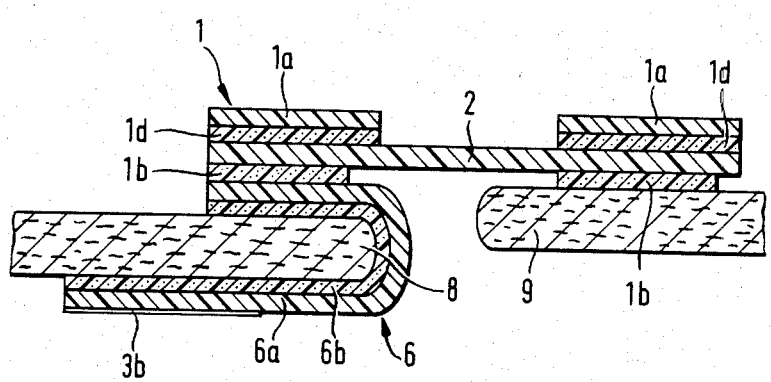

The invention will now be specified without limiting or restricting it in any way with reference to the drawings, in which FIG. 1 is a cross-section illustrating the basic design of a fastening in accordance with the invention, which is also applicable to the particular embodiments illustrated in FIGS. 2-4, each of which feature specific advantages relating to use and manufacture, and FIG. 2 illustrates a base (1a) that is made out of either a 20-40 $\mu$m-thick polyester film coated on both sides with 30-100 g/m$^2$ of pressure-sensitive adhesive (1b) consisting of a mixture of natural and/or synthetic rubber, tackifying resins, and an anti-ager plus reactive phenol resins, mineral fillers, and softeners if necessary, out of a 20-40 $\mu$m-thick PVC film coated on both sides with 30-100 g/m$^2$ of a pressure-sensitive adhesive (1b, 1d) consisting of a block co-polymer based on butadiene and styrene with tackifying resins and an anti-ager plus fillers and softeners if necessary, or out of a 20-40 monoaxially or biaxially stretched polypropylene film coated as specified in relation to the PVC film.

The intermediate elastic piece in FIG. 2 is a 50-100 $\mu$m-thick elastic polyurethane film, a 100-150 $\mu$m-thick film of a block co-polymer based on butadiene and styrene, or a knitted 100 g/m$^2$ elastic piece manufactured on a double rib loom. It may also consist of a approximately 100 $\mu$m-thick film of natural rubber.

The reinforcing strip 6 in FIG. 2 has a base 6a consisting of a 30-90 $\mu$m-thick, monoaxially stretched, pressure pre-treated film of polypropylene coated with 20-40 g/m$^2$ of a pressure-sensitive adhesive 6b. The adhesive is a mixture of a block co-polymer based on butadiene and styrene and tackifying resins, and anti-agers plus fillers and softeners if necessary. There is an adhesive-resistant layer 3b extending beyond adhesive 1b by 2-5 mm on the area of reinforcing strip 6 that lies under the end (1) of the adhesion strip that has a grip (1c). Adhesive-resistant layer 3b consists of 1 g/m$^2$ or less of a silicone resin. Adhesive-resistant layer 3b may also consist of a transition strip 3 (FIG. 1) on reinforcing strip 6.

The base 3a of transmission strip 3 in FIG. 1 consists of a 20-40$\mu$-thick polyester film coated on the side that is in contact with the adhesion end with 1 g/m$^2$ or less of a silicone resin 3b and on the other side with 30-50 g/m$^2$ of a pressure-sensitive adhesive 3c.

Pressure-sensitive adhesive 3c is a mixture of natural and/or synthetic rubber, tackifying resins, and anti-agers plus reactive phenol resins, mineral fillers, and softeners if necessary. Base 3a may however also consist of a 20-70 $\mu$m-thick, longitudinally stretched polypropylene foil that has been pressure pre-treated on both sides and is coated on the side that is in contact with the adhesion end with 1 g/m$^2$ or less of adhesive-resistant silicone resin 3b and on the other side with a pressure-sensitive adhesive 3c consisting of a mixture of a block co-polymer based on butadiene and styrene, tackifying resins, and anti-agers plus fillers and softeners if necessary.

Cover 4 in FIG. 2 consists of a 50-100 μm-thick base of paper of polypropylene film coated with an adhesive-resistant silicone resin.

Grip reinforcement 5 in FIG. 2 consists of a 50-80 μm-thick, longitudinally stretched, pressure pre-treated polypropylene film (Sa) coated with 20-50 g/m² of a pressure-sensitive adhesive 5b that consists of a mixture of natural rubber, tackifying resins, fillers, softeners, and anti-agers.

The cover 4, grip reinforcement 5, adhesive-resistant layer 3b, and reinforcing strip 6 in FIG. 3 are indentical to those illustrated in FIG. 2. Base 1a is a 100-150 μm-thick softened film of PVC coated with 30-100 g/m² of a pressure-sensitive adhesive 1b that consists of a mixture of natural and/or synthetic rubber, tackifying resins, and anti-agers plus reactive phenolic resins, mineral fillers, and softeners if necessary. An approximately 4 mm-wide strip of base 1a is not coated with adhesive and the PVC film is thermally bonded in this adhesive-free area to intermediate elastic piece 2 with a bond 7. In this case, the intermediate elastic piece is a 100-150 μm-thick elastic polyurethane film.

FIG. 4 illustrates an especially practical embodiment of the invention. Cover 4, reinforcing strip 6, adhesive-resistant layer 3b intermediate elastic base 2, and pressure-sensitive adhesive 1b are indentical to those illustrated in FIG. 2. Base 1a consists in this case of a strip of 100-150-g/m² paper or foam-coated polypropylene film. The adhesive 1d that attaches base 1a to intermediate elastic piece 2 may be for example a pressure-sensitive adhesive based on a block co-polymer of butadiene and styrene mixed with tackifying resins and anti-agers plus fillers and softeners if necessary.

FIG. 5 shows, in the sequence A-D, how a fastening in accordance with the invention may be employed. The schematically illustrated embodiment is that of FIG. 4. Cover (separation paper) 4 is first stripped off (A). The exposed pressure-sensitive adhesive 6b on the side without the grip is then pressed against one edge of the pants (B) and wrapped around it (C). The adhesion end (1) with grip 1c is then stripped along with base 1a and adhesive 1b and 1d from the surface of transition strip 3 with the separating layer 3b and adhesively fastened to the matching piece of the diaper pants (D).

We claim:

1. Self-adhesive elastic diaper-pants fastening with an adhesive-free intermediate elastic piece and non-elastic adhesion ends, characterized by
   (a) adhesion ends (1) with an intermediate elastic piece (2),
   (b) a base (1a), on which is mounted a pressure-sensitive adhesive (1b), in the vicinity of each adhesion end (1),
   (c) a strip that is free of pressure-sensitive adhesive and functions as a grip (1c) and (5) at the edge of one of the two bases (1a ),
   (d) a reinforcing strip (6) consisting of a base (6a) and a pressure-sensitive adhesive (6b),
   (e) an adhesive-resistant layer (3b) that is mounted either directly on the reinforcing strip (6) or by means of a transition strip (3) that consists of a base (3a) and pressure-sensitive adhesive (3c),
   (f) the adhesive-resistant layer (3b ) extending 2-5 mm on each side of the pressure-sensitive adhesive (1b) in the vicinity of the adhesion end (1) next to the grip (5), and
   (g) a cover (4) that extends over the whole width of the fastening.

2. Fastening as in claim 1, characterized in that the intermediate piece (2) consists of an elastic polyurethane film mixed with polymers, of a film of block co-polymers based on butadiene and styrene, of an elastic double-rib fabric, or of an elastic natural-rubber film.

* * * * *